(12) United States Patent
Feng et al.

(10) Patent No.: US 6,883,367 B2
(45) Date of Patent: Apr. 26, 2005

(54) METHOD FOR MEASURING ELASTIC PROPERTIES

(75) Inventors: Gang Feng, Mountain View, CA (US); Alfonso Hing Wan Ngan, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 34 days.

(21) Appl. No.: 10/300,323

(22) Filed: Nov. 20, 2002

(65) Prior Publication Data

US 2003/0094034 A1 May 22, 2003

Related U.S. Application Data

(60) Provisional application No. 60/331,751, filed on Nov. 20, 2001.

(51) Int. Cl.[7] .................................................. G01N 3/42
(52) U.S. Cl. ........................ 73/81; 73/78; 73/85; 73/76; 73/788
(58) Field of Search ............................. 73/78–85, 104, 73/10, 5, 760, 783, 787, 788, 826, 841, 847

(56) References Cited

U.S. PATENT DOCUMENTS

| | | | | |
|---|---|---|---|---|
| 3,969,928 A | * | 7/1976 | Zarka ........................... | 73/785 |
| 4,699,000 A | * | 10/1987 | Lashmore et al. ............. | 73/81 |
| 4,848,141 A | * | 7/1989 | Oliver et al. ................... | 73/81 |
| 5,133,210 A | * | 7/1992 | Lesko et al. ................... | 73/81 |
| 5,320,800 A | * | 6/1994 | Siegel et al. ................... | 419/66 |
| 5,999,887 A | * | 12/1999 | Giannakopoulos et al. ... | 702/33 |
| 6,053,034 A | * | 4/2000 | Tsui et al. ...................... | 73/81 |
| 6,134,954 A | * | 10/2000 | Suresh et al. .................. | 73/81 |
| 6,247,355 B1 | * | 6/2001 | Suresh et al. .................. | 73/82 |
| 6,311,135 B1 | * | 10/2001 | Suresh et al. ................. | 702/43 |
| 2003/0099495 A1 | * | 5/2003 | Look ..................... | 400/120.01 |

OTHER PUBLICATIONS

Kunert, Maik, "Mechanical Properties on Nanometer Scale and Their Relations to Composition and Microstructure", Apr. 28, 2000, Chapter 1, pp. 1–30.*

Wolf, Bodo, "Interference of Mechanical Properties from Instrumented Depth Sensing Indentation at Tiny loads and Indentation Depths", 2000, Journal of Crystal Research Technology, vol. 35, No. 4, pp. 377–399.*

Asif et al., "Quantitative Imaging of Nanoscale Mechanical Properties Using Hybrid Nanoindentation and Force Modulation", Aug. 1, 2001, Journal of Applied Physics, vol. 90, No. 3, pp. 1192–1200.*

Guo, Xiang–Dong, "Biomechanics and Remodeling of Trabecular Bone", 2001, Advances in Biomechanics, pp. 120–129.*

"Creep Adjusted Modulus of Elasticity", Downloaded from the Internet at http://www.tfhrc.gov/pavement/pccp/pdfs/valtm14.pdf.*

Dieter, George E., "Mechanical Metallurgy", 1986, pp. 432–470.*

* cited by examiner

*Primary Examiner*—Hezron Williams
*Assistant Examiner*—David A. Rogers
(74) *Attorney, Agent, or Firm*—Dickstein, Shapiro, Morin & Oshinsky, L.L.P.

(57) ABSTRACT

This invention relates to a method for measuring elastic modulus of a sample object. This invention also relates to a method for correcting creep effects in the modulus measurement. The error due to creep in the apparent contact compliance is equal to the ratio of the indenter displacement rate at the end of the load hold to the unloading rate. Determination of this error term and deduction of it from the measured contact compliance can be easily done at a low cost by modifying the data analysis software in any commercial depth-sensing indentation system.

19 Claims, 5 Drawing Sheets

METHOD FOR MEASURING ELASTIC PROPERTIES

CROSS-REFERENCE TO RELATED APPLICATION

This patent application claims priority to U.S. Provisional Patent Application No. 60/331,751 filed Nov. 20, 2001.

FIELD OF THE INVENTION

This invention relates generally to a method for measuring elastic properties of a material. More specifically, this invention relates to a method for measuring elastic modulus of a solid material by depth-sensing indentation. In addition, the present invention relates to a method for correcting for the effects of creep when measuring the elastic modulus of a solid material by depth-sensing indentation.

BACKGROUND OF THE INVENTION

Depth-sensing indentation systems have been used for measuring modulus of various materials. Most commercially available depth-sensing indentation systems are also known as "nanoindentators". When a nanoindentator is used, the indent size can be made to fall in the sub-micron range. As a result, ultra-small volumes of materials, e.g., second-phase particles in a matrix, thin-films deposited on substrates, etc., can be tested.

Unlike other conventional hardness testers, depth-sensing indentation systems use a depth-sensing machine to record the indenter displacement (or the "depth") data as the indentation proceeds. Many well-known brand names of commercial nanoindenters, such as those manufactured by MTS Systems Corporation, Hysitron Inc. and CSEM Instruments, all use the Oliver-Pharr scheme in their analysis packages. In the Oliver-Pharr scheme, the load and the depth data can be analyzed to give the contact area as well as the contact stiffness between the indenter and the sample. The contact area can be used to compute the hardness of the sample, while the contact stiffness can be used to compute the elastic modulus of the sample.

In the Oliver-Pharr scheme, the contact stiffness between the indenter tip and the sample is estimated in an unloading process from the peak load assuming that the material recovery during the unloading process is purely elastic. The reduced modulus $E_r$ for the contact between the indenter tip and the sample is calculated from the contact stiffness S at the onset of the unloading process as follows:

$$E_r = \frac{\sqrt{\pi}}{2} \frac{S}{\sqrt{A_c}} \quad (1)$$

wherein $A_c$ can be the contact area at full load. The contact area $A_c$ is calculated from the contact depth $h_c$ by assuming a shape function of the indenter, i.e., $$A_c = f(h_c),$$

$$h_c = h_{max} - \varepsilon \frac{P_{max}}{S} \quad (2)$$

wherein $\varepsilon$ is a constant depending on the indenter geometry (e.g., $\varepsilon$=0.75 for the Berkovich tip). The reduced modulus $E_r$ is related to the sample Young's modulus as follows:

$$\frac{1}{E_r} = \frac{1-v_s^2}{E_s} + \frac{1-v_t^2}{E_t} \quad (3)$$

wherein $E_s$=Young's modulus of the sample object, $v_s$=Poisson's ratio of the sample object, $E_t$=Young's modulus of the indenter tip, $v_t$=Poisson's ratio of the indenter tip. In the Oliver-Pharr scheme, the contact stiffness to be used in the above equations (1) and (2) is the observed (or apparent) contact stiffness S, at the onset of the unloading process.

In reality, however, significant creep can occur at the peak load even for metals at room temperature after long holding periods. As shown in FIGS. 2(a) and 2(b), the indenter displacement continues to creep in both cases even after a long holding period of ten (10) minutes. The displacement rate appears to settle to a steady value of about 0.020 nm/s in Al and about 0.009 nm/s in Ni$_3$Al. Such a significant creep effect at the peak load can strongly affect the subsequent unloading behavior, especially when the unloading rate is not high enough.

In the extreme case where a creep dominates an elastic recovery at the onset of the unloading process, the load-displacement curve can even exhibit a "nose", such as shown in FIG. 4a for an aluminum sample object. Load schedules (i) to (iii), such as those shown in FIG. 3b, represent three similar indentation experiments on the same aluminum sample. Load schedule (i) has a very rapid unloading rate. Load schedules (ii) and (iii) have the same unloading rate, which is slower than the unloading rate in load schedule (i). On the other hand, load schedules (i) and (ii) have a short load holding period before the unloading process, while load schedule (iii) has a longer load holding period. A conspicuous "nose", such as that shown in FIG. 4a, appears in the unloading curve for load schedule (ii). The "nose" disappears when the unloading rate is increased, such as shown in the unloading curve for load schedule (i), or when the load holding period before unloading is lengthened, such as shown in the unloading curve for load schedule (iii).

When a "nose" occurs, the elastic modulus cannot be accurately calculated using the Oliver-Pharr scheme, because the apparent contact stiffness $S_u$ becomes negative. Moreover, even if a "nose" does not occur, the presence of creep can cause serious errors in the estimation of the elastic modulus, if the creep effect is not corrected. Moreover, creep effects can become significant in certain circumstances, such as where an indentation is performed at a temperature of a significant fraction (e.g., more than 40%) of the absolute melting temperature or where a nano-sized indentation is performed by exerting a very large pressure on the sample.

The present invention provides a method for measuring elastic properties, such as the elastic modulus of an object, that avoids the above problems. Moreover, the present invention provides a method for measuring the elastic modulus of a solid material by depth-sensing indentation where the creep effect is corrected. Furthermore, the present invention provides a method for correcting a creep effect occurred when measuring elastic properties of a solid material by depth-sensing indentation.

SUMMARY OF THE INVENTION

This invention provides a method for measuring elastic properties of an object, such as by depth-sensing indentation. The present invention also provides a method for correcting for the effects of creep occurred in measuring the elastic modulus of various materials by depth-sensing indentation. The method can comprise defining a correction term in the contact compliance between an indenter tip and an object to be measured. In one embodiment, the correction term can be defined by equation (4) below. The method can also comprise quantifying the correction term by measuring the related quantities from the indentation data. In one embodiment, curve fitting can be employed in quantifying the correction term. The creep correction term can be removed from the apparent contact compliance in the calculation of the sample modulus. Such a correction procedure can be incorporated easily into the analysis software of any existing depth-sensing indentation system based on the Oliver-Pharr scheme.

BRIEF DESCRIPTION OF THE DRAWINGS

These and other features, aspects, and advantages of the invention will become much more apparent from the following description and accompanying drawings, in which:

FIGS. 3a and 3b show load schedules used in the experiments, in which FIG. 3b shows the three different load schedules used on a sample material of aluminum;

DETAILED DESCRIPTION OF THE INVENTION

Figure 1A:
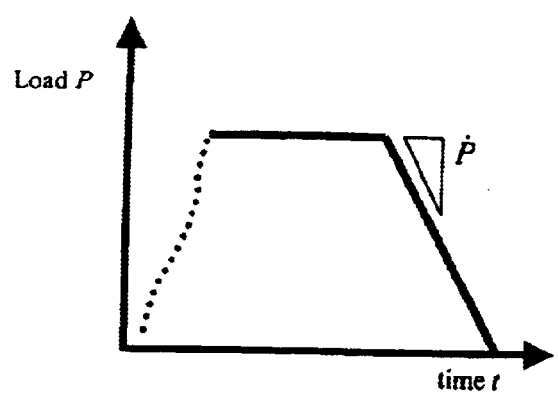
FIGS. 1a to 1c show the P-t curve, the h-t curve, and the P-h curve respectively in one embodiment of the invention for modulus measurement using depth-sensing indentation.

Exemplary methods embodying the principles of the present invention are shown throughout the drawings and described in the various embodiments below.

The invention is contemplated to measure various properties of various materials. For example, the invention can measure the elastic properties, such as elastic modulus of a sample material. In the method of the invention, one or more correction term can be obtained and used to correct one or more measurement errors occurred during the measurement of the sample material properties. In one embodiment, a depth-sensing indentation system can be used for measuring the elastic modulus of a sample material. In such an embodiment, the contact stiffness between the depth-sensing indenter and the sample material, after correcting for the effects of creep, can be obtained and used as a corrected term. In another embodiment, one or more corrected terms can be used to obtain the properties, such as the elastic modulus, of the sample material.

According to one aspect of the invention, a method is provided to measure elastic properties of various materials using one or more corrected terms. Additionally or alternatively, the method can comprise quantifying the corrected terms.

In one embodiment, a method is provided to measure the elastic modulus of a material during the unloading process in depth-sensing indentation. The method can comprise one or more of the following:
(a) measuring the indenter displacement drift rate $\dot{h}_h$ just prior to the unloading process;
(b) measuring the apparent contact stiffness $S_u$ (the rate of change of load with respect to indenter displacement) at the onset of the unloading process;
(c) obtaining the contact stiffness S based on one or more of the indenter displacement drift rate $\dot{h}_h$, the apparent contact stiffness $S_u$, and $\dot{P}$, wherein $\dot{P}$ is the imposed unloading rate at the onset of the unload process;
(d) using the value of S obtained from step (c) to calculate the contact area $A_c$ based on equation (2); and
(e) using the value of S obtained from step (c) above and the value of A, from step (d) above to calculate the reduced modulus $E_r$ based on equation (1).

According to another aspect of the invention, a method is provided to correct various measurement errors, such as occurred when measuring various properties of a sample material. In an embodiment where a depth-sensing indentation system is used for measuring the elastic properties of a sample material, the method of the invention is capable of correcting various measurement errors, such as caused by creep and/or thermal drift, as will be described in details below.

In one embodiment, a method is provided to correct various measurement errors during an unloading process in depth-sensing indentation. The method can comprise one or more of the following:
(a) measuring the indenter displacement drift rate $\dot{h}_h$ just prior to the unloading process;
(b) measuring the apparent contact stiffness $S_u$ (the rate of change of load with respect to indenter displacement) at the onset of the unloading process; and
(c) obtaining a correction term based on one or more of $\dot{h}_h$, $S_u$, and $\dot{P}$, wherein $\dot{P}$ is the imposed unloading rate at the onset of the unload process.

In an embodiment where the measurement is carried out by using a depth-sensing indentation system, the correction term can concern the contact stiffness and/or the contact area as will be described in details below.

Figure 1B:
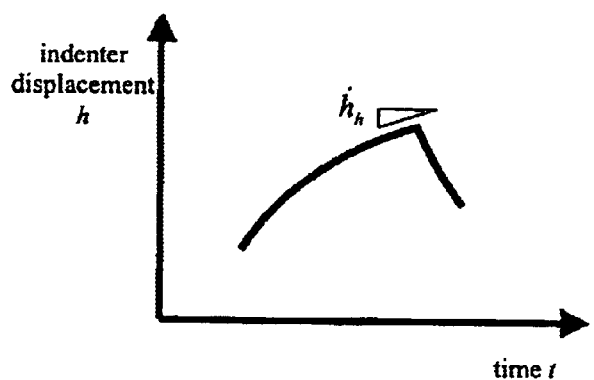
Figure 1C:
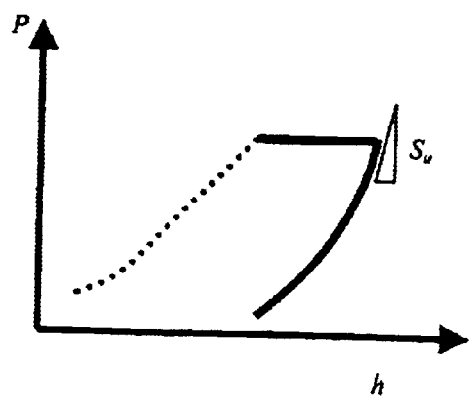

The contact stiffness S can be obtained in various manners. For example, the contact stiffness S can be obtained by taking one or more of the following factors into consideration: the observed (or apparent) contact stiffness $S_u$, the indenter displacement rate $\dot{h}_h$, and the unloading rate $\dot{P}$. In an exemplary embodiment, the contact stiffness S to be used in equation (1) can be given by the following equation:

$$\frac{1}{S} = \frac{1}{S_u} + \frac{\dot{h}_h}{|\dot{P}|} \quad (4)$$

wherein the correction term is capable of correcting creep and/or thermal drift. In an exemplary embodiment such as shown in FIG. 1, $\dot{h}_h$ can be the indenter displacement rate recorded at the end of the load holding period preceding the unloading process. In another exemplary embodiment, $\dot{P}$ can be the unloading rate at the onset of the unloading process. In a further exemplary embodiment, $S_u$ can be the contact stiffness at the onset of the unloading process. The observed (or apparent) contact stiffness. So, the indenter displacement rate $\dot{h}_h$, and/or the unloading rate $\dot{P}$ will be described in detail below.

In one embodiment, to evaluate the apparent contact stiffness $S_u$ at the onset of the unloading process from the unloading portion of the load-displacement P-h curve, the load-displacement P-h curve can be first fitted by the following equation:

$$h = h_o + A_1 P^m + A_2 P^n \quad (5)$$

wherein $h_0$, $A_1$, $A_2$, m, and n can be fitting constants. For example, $h_0$ can be about 520.55±0.15; $A_1$ can be about 0.254±0.003; $A_2$ can be about 7.7E-23±4.8E-22; m can be about 0.5; and/or n can be about 5.90±0.71. Equation (5) can provide very good fit to the onset portion of the unloading process. In another exemplary embodiment, $R^2$ can be about 0.97785. In one exemplary embodiment, the curve fitting of the load-displacement P-h curve can be carried out during an initial part of the unloading process. In another embodiment, the contact stiffness at the onset of the unloading process can be defined as $S_u = dP/dh|_u$, wherein "u" denotes the onset of the unloading process. In an exemplary embodiment, $S_u$ can be calculated, such as by differentiating equation (5).

In another embodiment, the indenter displacement rate $\dot{h}_h$ in equation (4) can be obtained by fitting the displacement-time h-t curve during the load holding period or prior to the unloading process by the following empirical law:

$$h(t) = h_I + \beta(t - t_I)^{1/3} + Kt \quad (6)$$

where $h_I$, $\beta$, $t_I$, and K can be fitting constants. For example, $h_I$ can be about 568.66±0.03; $\beta$ can be about 2.94±0.01, $t_I$ can be about 237.32±0.05; and/or K can be about 0.0062±0.0001. Alternatively, $h_I$ can be about 184.754±0.022; $\beta$ can be about 1.320±0.010, $t_I$ can be about 274.927±0.096; and/or K can be about 0.00315±0.00009. The above equation is capable of providing very good fittings to the displacement-time h-t curves. In an exemplary embodiment, $R^2$ can be about 0.99753. In another exemplary embodiment, $R^2$ can be about 0.99013. In one embodiment, the indenter displacement rate $\dot{h}_h$ can be obtained as follows: $\dot{h}_h = dh/dt|_h$, wherein "h" can denote the end of the load holding period. In a further embodiment, the indenter displacement rate $\dot{h}_h$ can be obtained by differentiating equation (6). It will be appreciated that various alternate embodiments of calculating the contact stiffness S, the observed (or apparent) contact stiffness $S_u$, the indenter displacement rate $\dot{h}_h$, and/or the unloading rate $\dot{P}$ are within the scope of the invention.

Additionally or alternatively, the correction term can be based in part on the contact depth $h_c$. In an exemplary embodiment, the contact depth $h_c$ can be determined from the Oliver-Pharr scheme after thermal drift correction and contact stiffness correction due to creep effects. In another exemplary embodiment, the corrected contact stiffness S obtained from the above equation (4) can be used in equation (2) to obtain a contact depth $h_c$. The corrected contact depth $h_c$ can then replace the uncorrected contact depth to obtain the elastic modulus of the sample material as in the Oliver-Pharr scheme. It will be appreciated that various alternate embodiments of obtaining the contact depth $h_c$ are within the scope of the invention.

Figure 2A:
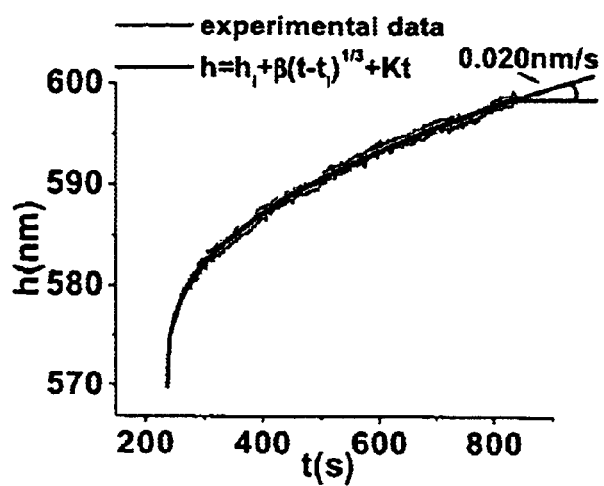
FIGS. 2a and 2b are the displacement-time curves of the load holding process after correction of thermal drift in (a) Al, load=2918.1±1.5 $\mu$N and (b) Ni$_3$Al (111), load=4964.6±2.1 $\mu$N, respectively.
Figure 2B:
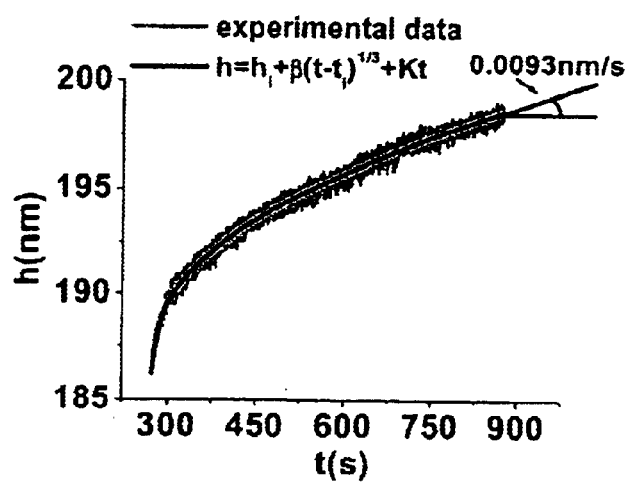

The method of the invention will now be described through the various experiments. The invention can be used to measure elastic properties of various materials. In the embodiments such as shown in FIGS. 1 and 2, the following three materials can be used: a single crystal of $Ni_3Al$, a single crystal of copper, and a polycrystalline Al. In an exemplary embodiment, the $Ni_3Al$ single crystal can have various compositions. For example, the composition of the $Ni_3Al$ single crystal can be of about 75 at. % Ni, about 16.7 at. % Al, about 8.0 at. % Cr, and about 0.3 at. % B. In another exemplary embodiment, the copper single crystal can have a purity of up to 99.99%. In a further exemplary embodiment, the polycrystalline Al can have a grain size of approximately 1 to 2 mm. It will be appreciated that various alternate embodiments of sample materials are within the scope of the invention.

Optionally, the sample materials can be subjected to various processes prior to the measurement. In one embodiment, the crystal material can be homogenised prior to nanoindentation. For example, the crystal can be homogenised at about 1250° C. for about 120 hours. In another embodiment, the copper single crystal can be annealed for about 5 hours at about 800° C. In a further embodiment, the polycrystalline Al can be in the as-cast state. It will be appreciated that various alternate embodiments of processing the sample materials are within the scope of the invention.

In one embodiment, the indentation surfaces of the various sample objects can be prepared by various methods. For example, the crystal materials can be prepared by having their (111) surface for indentation cut by various means. In an exemplary embodiment, the $Ni_3Al$ or the Cu crystal can have its (111) surface for indentation cut such as by a spark machine. Additionally or alternatively, the (111) surface for indentation can be subjected to various processes, such as grinding and electropolishing. In one embodiment, the Al surfaces can be electropolished. It will be appreciated that various alternate embodiments of processing the indentation surfaces of the sample materials are within the scope of the invention.

The indentation process can be carried out using various conventional indentation equipment. For example, the indentation process can be carried out with nanoindenters or atomic force microscopy (AFM) setups with a Berkovich tip, such as those manufactured by Hysitron Inc. or TM Microscopes. In one exemplary embodiment, the indentation process can be carried out at room temperature.

Figure 3A:
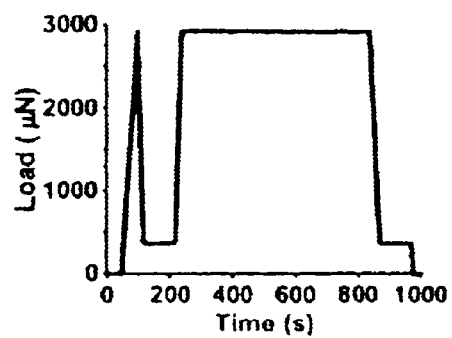
Figure 3B:
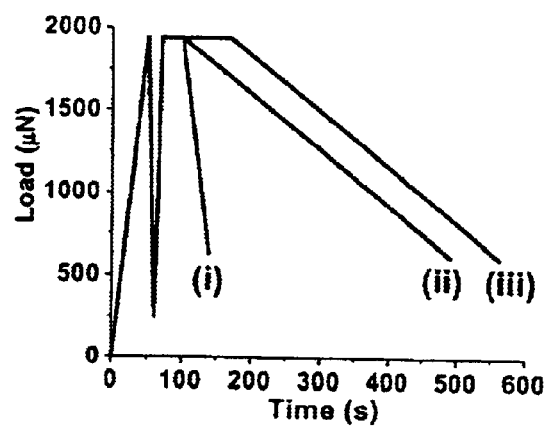

Various load schedules can be employed in the indentation process. For example, the load schedules can be similar to that as shown in FIG. 3a or FIG. 3b. In one embodiment, the load can be ramped up quickly to the peak value. In an exemplary embodiment, the load can reach its peak value within a short period of time, such as within about 50 seconds. The peak value of the load can vary depending on the sample material. For example, the peak value of the load can be from about 3000 $\mu$N to about 5000 $\mu$N. In one exemplary embodiment, the peak load value for Al can be 2918.1±1.5 $\mu$N. In another exemplary embodiment, the peak value for $Ni_3Al$ (111) can be 4964.6±2.1 $\mu$N.

In another embodiment, the load can be held at its peak value for a predetermined period of time. In an exemplary embodiment, the load holding period can be up to about 100 seconds. In another exemplary embodiment, the load holding period can be more than 50 seconds. In a preferred embodiment, the load can be ramped up quickly to the peak value followed by a rapid unloading process. Such a load schedule is capable of initiating the indent shape so that time-independent plasticity can be made negligible in subsequent stages.

In a further embodiment, the load can be ramped up again to the peak value after the initial unloading process. In an exemplary embodiment, the load can be held for a load holding period after being ramped up again to the peak value. The contact stiffness S for modulus calculation can be measured from the final unloading process. It will be appreciated that various alternate embodiments of load schedules of the indentation process are within the scope of the invention.

Various methods can be adopted to correct the measurement error caused by thermal drift. In one embodiment, low-load holds can be applied to the sample material during the indentation process. In an exemplary embodiment, low-load holds, such as about 15% of the peak load, can be placed towards the end of the final unloading process. In anther exemplary embodiment, low-load holds can be placed between the cycles to measure the thermal drift rate. Such low-load holds can be used to assess the fluctuation of the thermal drift rate during the entire measurement. For example, when the thermal drift rate changes beyond a predetermined value during the measurement, the results gathered under such circumstances can be discarded.

Creep effects can have significant impact on the modulus measured. For example, the following creep factor C can be used to represent the importance of creep over elasticity:

$$C = \frac{\dot{h}_h^c S}{|\dot{P}|} \tag{7}$$

wherein $\dot{h}_h^c$ is the creep portion of $\dot{h}_h$. In an exemplary embodiment, $\dot{h}_h^c$ can be obtained by subtracting the thermal drift rate from $\dot{h}_h$. According to equation (7), a large creep factor C can result from a slow unloading rate and/or a short load holding period, which can cause a high creep displacement rate at the end of the load holding period.

Figure 4A:
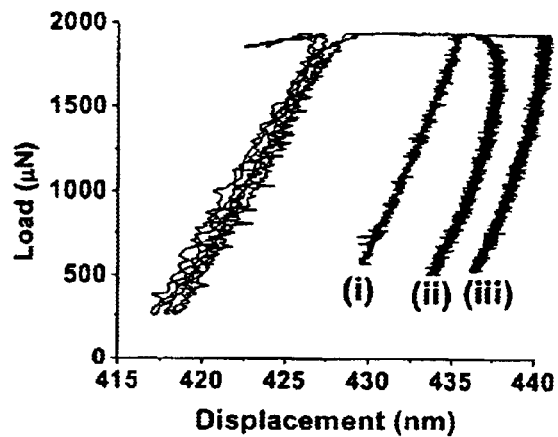
FIG. 4a is an enlarged view of the unloading portions of the load-displacement curves showing creep effects thereon after correcting thermal drift in aluminum.
Figure 4B:
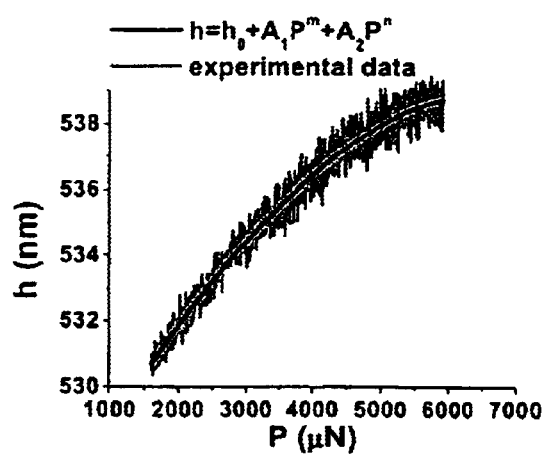
FIG. 4b illustrates the fitting by equation (5) of the unloading curve for Cu (111) with large creep effects, wherein unloading rate=12.47 $\mu$N/s, and creep factor C=60.3%.

FIG. 4b shows a "nose" occurrence in the load-displacement P-h curve during an unloading process in Cu. The indentation conditions can be such that the creep factor defined in equation (7) can be about 60% so that the creep effect is significant. According to one embodiment of the invention, equation (5) can provide very good fit to the onset portion of the unloading process. In an exemplary embodiment, the value of $S_u$ fitted by equation (5) can be about 3454 µN/nm. In another exemplary embodiment, $R^2 = 0.97785$.

Figure 5A:
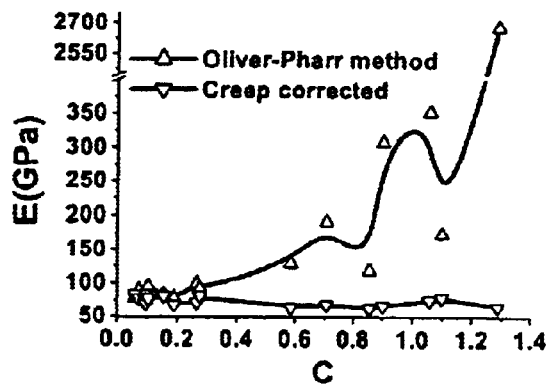
FIGS. 5a to 5c show different modulus-creep factor curves obtained by the Oliver-Pharr scheme and the invention for sample materials of (a) Al, (b) Cu (111), and (c) Ni$_3$Al (111), respectively.
Figure 5B:
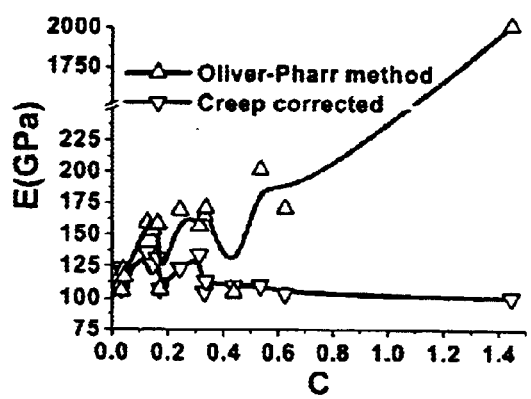
Figure 5C:
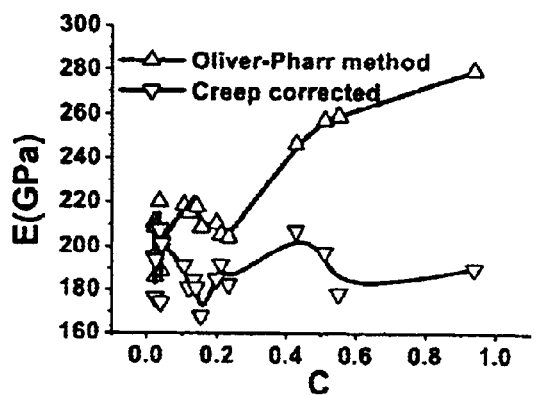

FIGS. 5a to 5c show modulus-creep factor E-C curves containing modulus data measured from three sample materials. The creep factors C in FIGS. 6a to 5c can be defined by equation (7). All modulus results shown in FIGS. 5a to 5c, whether corrected for creep or not, have been corrected for thermal drift and machine compliance. As shown in FIGS. 5a to 5c, modulus values obtained without correcting for the effects of creep increase when the creep factor C increases. For example, the apparent modulus for Al and Cu is dramatically high, such as over 2000 GPa, when the creep factor C is higher than about 1.4.

FIGS. 5a to 5c also show the modulus values obtained based on equations (1) and (2) wherein the contact stiffness S is corrected by equation (4). After the creep effect is corrected by equation (4), the calculated modulus values tend towards a constant value. According to one embodiment, the corrected modulus is about 72.3±7.5 GPa for Al, about 116.9±11.1 GPa for Cu, and about 189.9±11.9 GPa for Ni$_3$Al. The theoretical values of the reduced modulus calculated using the method of Vlassak and Nix are 74.8 GPa for polycrystalline Al, 125.9 GPa for Cu (111), and 201.9 GPa for Ni$_3$Al (111). Such theoretical values of the reduced modulus all fall within the corresponding modulus value ranges measured by the method of the invention.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being not limited to the foregoing description.

What is claimed is:

1. A method for measuring the contact stiffness during an unloading process in depth-sensing indentation, comprising:
   measuring the indenter displacement drift rate h$_h$ just prior to the unload process;
   measuring the apparent contact stiffness S$_u$ at the onset of the unloading process; and
   obtaining the contact stiffness S based on one or more of the indenter displacement drift rate h$_h$, the apparent contact stiffness S$_u$, and P;
   wherein P is the imposed unloading rate at the onset of the unload process.

2. The method of claim 1, wherein the contact stiffness S is obtained based on the following equation:

$$\frac{1}{S} = \frac{1}{S_u} + \frac{\dot{h}_h}{|\dot{P}|}.$$

3. The method for obtaining a correction term for correcting for the effects of creep, comprising determining a correction term based in part on one or more of the indenter displacement drift rate h$_h$, the apparent contact stiffness S$_u$, and the imposed unloading rate P wherein:
   the indenter displacement drift rate h$_h$, is measured prior to the unloading process;
   the apparent contact stiffness S$_u$ is measured at the onset of the unloading process; and
   the imposed unloading rate P is measured at the onset of the unloading process.

4. The method of claim 3, wherein the correction term comprises a first correction term, which is based in part on a contact stiffness S.

5. The method of claim 4, wherein the contact stiffness S is obtained by the following equation:

$$\frac{1}{S} = \frac{1}{S_u} + \frac{\dot{h}_h}{|\dot{P}|}.$$

6. The method of claim 3, wherein the correction term is based in part on a contact depth h$_c$.

7. The method of claim 4, wherein the correction term further comprises a second correction term based in part on one or more of the following: the maximum indenter displacement, the indenter geometry, the maximum load imposed, the apparent contact stiffness measured at the onset of the unloading process, the indenter displacement drift rate measured prior to the unloading process, and the imposed unloading rate measured at the onset of the unloading process.

8. The method of claim 6, wherein the second correction term is based in part on the contact depth $h_o$.

9. The method of claim 8, wherein the contact depth $h_c$ is obtained based on the following equation:

$$h_c = h_{\max} - \varepsilon P_{\max}\left(\frac{1}{S_u} + \frac{\dot{h}_h}{|\dot{P}|}\right)$$

wherein $h_{max}$ is the maximum indenter displacement, $\varepsilon$ is a constant depending on the indenter geometry, $P_{max}$ is the maximum load imposed, $S_u$ is the apparent contact stiffness measured at the onset of the unloading process, $\dot{h}_h$ is the indenter displacement drift rate measured prior to the unloading process, and $\dot{P}$ is the imposed unloading rate measured at the onset of the unloading process.

10. The method of claim 3, wherein the indenter displacement drift rate $\dot{h}_h$ is obtained by curve fitting of the data of indenter displacement-time h-t curve prior to the unloading process by the following equation:

$$h(t)=h_i+\beta(t-t_i)^{1/3}+Kt$$

wherein $h_i$, $\beta$, $t_i$, and $K$ are fitting constants.

11. The method of claim 3, wherein the apparent contact stiffness Su is obtained by curve fitting of the data of load-indenter displacement P-h curve during an initial part of the unloading process by the following equation:

$$h=h_o \pm A_1 P^m + A_2 P^n$$

wherein $h_o$, $A_1$, $A_2$, m, and n are fitting constants.

12. A method for correcting for the effects of creep in the measurement of a material property during an unloading process in the depth-sensing indentation, comprising:
measuring the indenter displacement drift rate $\dot{h}_h$ prior to the unloading process;
measuring the apparent contact stiffness $S_u$ at the onset of the unloading process;
measuring the imposed unloading rate $\dot{P}$ at the onset of the unload process;
obtaining a correction term based on one or more of the indenter displacement drift rate $\dot{h}_h$, the apparent contact stiffness $S_u$, and $\dot{P}$; and
determining a corrected material property using the correction term.

13. The method of claim 12, wherein the correction term comprises a contact stiffness S.

14. The method of claim 13, wherein the contact stiffness is calculated according to the following equation:

$$\frac{1}{S} = \frac{1}{S_u} + \frac{\dot{h}_h}{|\dot{P}|}.$$

15. The method of claim 13, further comprising obtaining a second correction term.

16. The method of claim 15, wherein the second correction term is based in part on one or more of the following: the maximum indenter displacement, the indenter geometry, the maximum load imposed, the apparent contact stiffness measured at the onset of the unloading process, the indenter displacement drift rate measured prior to the unloading process, and the imposed unloading rate measured at the onset of the unloading process.

17. The method of claim 15, wherein the second correction term is based in part on the contact depth $h_o$ based on the following:

$$h_c = h_{\max} - \varepsilon P_{\max}\left(\frac{1}{S_u} + \frac{\dot{h}_h}{|\dot{P}|}\right)$$

wherein $h_{max}$ is the maximum indenter displacement, $P_{max}$ is the maximum load imposed, $\varepsilon$ is a constant depending on the indenter geometry, $S_u$ is the apparent contact stiffness measured at the onset of the unloading process, $\dot{h}_h$ is the indenter displacement drift rats measured prior to the unloading process, and $\dot{P}$ is the imposed unloading rate measured at the onset of the unloading process.

18. The method of claim 14, wherein the indenter displacement drift rate $\dot{h}_h$ is obtained by curve fitting of the data of indenter displacement-time h-t curve prior to the unloading process by the following equation:

$$h(t)=h_i+\beta(t-t_i)^{1/3}+Kt$$

wherein $h_i$, $\beta$, $t_i$, and $K$ are fitting constants.

19. The method of claim 14, wherein the apparent contact stiffness $S_u$ is obtained by curve fitting of the data of load-indenter displacement P-h curve during an initial part of the unloading process by the following equation:

$$h=h_o \pm A_1 P^m + A_2 P^n$$

wherein $h_o$, $A_1$, $A_2$, m, and n are fitting constants.

* * * * *